United States Patent [19]

Klieger et al.

[11] 4,032,567

[45] June 28, 1977

[54] TRIIODOISOPHTHALIC ACID MONOAMINO ACID AMIDES, PROCESS FOR THE PREPARATION THEREOF, AND USE THEREOF AS X-RAY CONTRAST MEDIA

[75] Inventors: Erich Klieger; Wolfgang Beich; Eberhard Schroder, all of Berlin, Germany

[73] Assignee: Schering Aktiengesellschaft, Berlin & Bergkamen, Germany

[22] Filed: Mar. 3, 1975

[21] Appl. No.: 555,043

Related U.S. Application Data

[62] Division of Ser. No. 331,110, Feb. 9, 1973, Pat. No. 3,953,501.

[30] Foreign Application Priority Data

Feb. 16, 1972 Germany .......................... 2207950

[52] U.S. Cl. .................. 260/519; 260/112.5 R; 260/247.1 H; 260/247.2 A; 260/268 C; 260/309; 260/326.14 T; 260/326.2; 260/516; 260/558 S; 260/558 A; 260/518 A; 260/326.41
[51] Int. Cl.² .............................. C07C 101/68
[58] Field of Search ... 260/471 A, 518 A, 247.1 H, 260/247.2 A, 268 C, 309, 326.2, 326.43, 516, 519, 558 S, 558 A, 326.41

[56] References Cited

UNITED STATES PATENTS

| | | | |
|---|---|---|---|
| 3,453,322 | 7/1969 | Obendorf et al. | 260/471 A |
| 3,666,760 | 5/1972 | Ackerman | 260/471 A |
| 3,853,965 | 12/1974 | Ackerman | 260/471 A |
| 3,890,318 | 6/1975 | Obendorf et al. | 260/471 A |

*Primary Examiner*—Paul J. Killos
*Attorney, Agent, or Firm*—Millen & White

[57] ABSTRACT

New amino acid derivative of acylamino-5-alkylcarbamoyl-2,4,6-triiodobenzoic acids are described together with processes for their preparation and use and novel intermediates useful in preparing these compounds. The compounds are valuable radiopaque agents useful as X-ray contrast media.

9 Claims, No Drawings

4,032,567

TRIIODOISOPHTHALIC ACID MONOAMINO ACID AMIDES, PROCESS FOR THE PREPARATION THEREOF, AND USE THEREOF AS X-RAY CONTRAST MEDIA

This is a division, of application Ser. No. 331,110 filed Feb. 9, 1973, now U.S. Pat. No. 3,953,501.

BACKGROUND OF THE INVENTION

This invention relates to triiodoisophthalic acid monoamino acid amides (amino acid derivatives of the acylamino-5-alkylcarbamoyl-2,4,6-triiodobenzoic acids), processes for the preparation thereof, and the use thereof as radiopaque agents, especially as X-ray contrast media for illustrating the urinary tract system, the cardiovascular system and the body cavities containing cerebrospinal fluid.

3-acylamino-5-alkylcarbamoyl-2,4,6-triidobenzoic acids are known from U.S. Pat. No. 3,145,197. Several amino acid derivatives of 3-acylamino-5-alkylcarbamoyl-2,4,6-triiodobenzoic acids have likewise been described, e.g., 5-acetamido-2,4,6-triiodoisophthaloyl diglycine in U.S. Pat. No. 3,102,880 and N-[3-N-(alkyl-acylamino)-5-alkylcarbamoyl-2,4,6-triiodobenzoyl]-amino acids in Helv. Chim. Acta 54 (8): 2551–2559 (1971). Although these compounds have a low toxicity, they have several undesirable side effects. For example, they do not meet the high requirements to be fulfilled by a medium for myelography, e.g., see Ugeskirft for laeger 134 (18): 936 (1972) and Advances in X-Ray Technology 115 : 683–684 (1971). A primary requirement for radiopaque agents useful in myelography is the cisternal compatibility.

OBJECTS OF THE INVENTION

Accordingly, it is a general object of this invention to provide new amino acid derivatives of the acylamino-5-alkylcarbamoyl-2,4,6-triiodobenzoic acids and methods for their preparation and use.

Another object of this invention is to provide novel intermediates useful in the production of triidoisophthalic acid monoamino acid amides.

A further object of this invention is to provide useful radiopaque compositions and methods for their use.

Upon further study of the specification and appended claims, further objects and advantages of this invention will become apparent to those skilled in the art.

SUMMARY OF THE INVENTION

Briefly, the above and other objects are attained in accordance with one aspect of this invention by providing a triiodoisophthalic acid monoamino acid amide of the Formula E

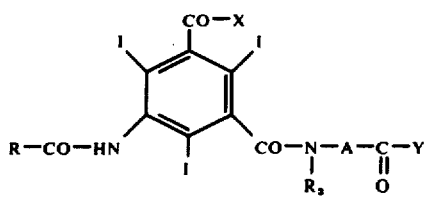

wherein

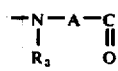

A is a divalent amino lower alkanoyl,

R is lower alkyl, hydroxyalkyl or alkoxyalkyl,

X and Y are different from each other and each represent hydroxy or

wherein $R_1$ and $R_2$ are each hydrogen, lower alkyl or hydroxyalkyl, or $R_1$ and $R_2$ together with the nitrogen atom form a 5 to 7 member heterocyclic ring which can contain a further oxygen, nitrogen or sulfur hetero atom, and $R_3$ is hydrogen, methyl, ethyl or phenyl and the physiologically acceptable salts thereof.

In another aspect of this invention, compounds of Formula E are prepared by N-acylating a novel compound of the Formula Z:

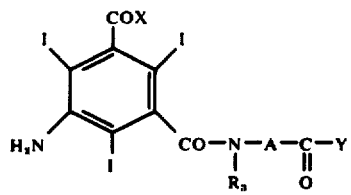

wherein A, X and Y have the above-indicated values, with an amino acylating agent of the formula R—C-O—W wherein R has the above-indicated values and W is a carboxylic acid functional group.

DETAILED DISCUSSION

It has now been found that the amino acid derivatives of this invention possess a high physiological compatibility and are highly suitable not only for uro- and angiography, but also for myelography.

The divalent aminoloweralkanoyl radical A is derived from an aminocarboxylic acid, which can assume any desired configuration. One or two amino groups can be disposed in any desired position, although the α-aminocarboxylic acids are preferred. Furthermore, the aminocarboxylic acids can also be unsaturated, branched, polybasic, and substituted in the usual manner, for example, by hydroxy groups, mercapto groups, optionally substituted aryl, cycloalkyl or heterocyclic groups. Also, the amino group can be substituted by aliphatic, aromatic or mixed aromatic-aliphatic groups.

Suitable aminocarboxylic acids include but are not limited to glycine, sarcosine, alanine, N-phenylalanine, N-benzylalanine, valine, leucine, isoleucine, serine, threonine, aminobutyric acid, cysteine, methionine, ornithine, lysine, aspartic acid, glutamic acid, asparagine, glutamine, arginine, phenylalanine, tyrosine, proline, hydroxyproline, tryptophan and histidine as well as β-amino acids, e.g., β-alanine, or oligopeptides, e.g., glycyl glycine, glycyl L-leucine, etc. Of these, preferred are glycine, sarcosine, alanine, valine, leucine, serine, threonine and proline.

The alkyl, hydroxyalkyl, alkoxy and alkanoyl residues when present are preferable lower residues, e.g., lower alkyl of 1–6 carbon atoms, preferably 1–4 carbon atoms such as methyl, ethyl, propyl, isoproyl or butyl; hydroxyalkyl of 1–6 carbon atoms, preferably 1–4 carbon atoms, e.g., hydroxymethyl, hydroxyethyl or hydroxypropyl; lower alkoxy of 1-4 carbon atoms, preferably 1-2 carbon atoms such as methoxy or ethoxy; lower alkanoyl of 1-6 carbon atoms, and especially lower alkanoyl of 1-4 carbon atoms such as acetyl, propionyl, butyryl and isobutyryl.

When $R_1$ and $R_2$ together with the nitrogen atom form a heterocyclic ring, preferred are those of pyrrolidine, morpholine or piperazine.

The compounds of this invention according to Formula E include both the free compounds and their metal, ammonium and amine salts, preferably the water-soluble and non-toxic physiologically acceptable salts, although water-insoluble and/or toxic salts can readily be used for isolation and/or characterization purposes. These compounds, individually, or in admixture, are valuable radiopaque agents.

Suitable salts of physiologically compatible bases includes but are not limited to the alkali metal salts, e.g., sodium and potassium; the alkaline earth metal salts, e.g., calcium and magnesium; amine salts, e.g., ammonium, heterocyclic amines, e.g., morpholine and N-alkyl amines, hydroxyalkylamines, alkyl(hydroxyalkyl) amines and di(hydroxyalkyl)amines, wherein alkyl in each instance preferably contains 1-6, more preferably 1-4 carbon atoms, e.g., methyl, ethyl, n-propyl, isopropyl, n-butyl, isobutyl, tert.-butyl, including trimethylamine, diethylamine, ethanolamine, diethanolamine and polyhydroxyalkylamines, e.g., trihydroxy-tert.-butylamine, saccharidyl amines, including glucamine, N-monoalkylglucamines and N,N-dialkylglucamines. Preferred mono- and dialkyl glucamines are those compounds which contain, in one or both alkyl groups respectively, a total of one to four carbon atoms. Especially preferred alkylglucamine salts are the N-methyl and N,N-dimethyl salts. The salts can be employed alone or in admixture, e.g., an alkali metal salt can be partially replaced by a corresponding alkaline earth metal salt.

Equivalents of the compounds of this invention are compounds otherwise corresponding structurally thereto and possessing the same activity where instead of a loweralkanoyl group that is present the acyl group of another organic acid, e.g., a carboxylic-acid containing up to 15 carbon atoms, especially intermediate (7-12) aliphatic carboxylic, preferably an alkanoic acid, which can be unsaturated, branched polybasic, or substituted in the usual manner, e.g., by hydroxy or halogen atoms; a cycloaliphatic, aromatic and mixed aromatic-aliphatic (alkaryl and aralkyl) acid, which can likewise be substituted in the usual manner, examples of such equivalents being caproic acid, enanthic acid, undecyclic acid, oleic acid, trimethylacetic acid, dichloroacetic acid, cyclopentylpropionic acid, phenylpropionic acid, phenylacetic acid, phenoxyacetic acid, succinic acid, benzoic acid; other examples being α-ethylbutyric, valeric, isovaleric, α-ethylvaleric, 2-methylbutyric, 3-ethylbutyric, hexanoic, diethylacetic, triethylacetic, enanthic, octanoic, undecyclic and palmitic acid; cyclic acids, preferable a cycloaliphatic acid containing 5-18 carbon atoms, e.g., cyclopropylideneacetic, cyclobutylcarboxylic, cyclopentylcarboxylic, cyclopentylacetic, cyclohexyl carboxylic, cyclohexylacetic and β-cyclohexylpropionic acid; carbocyclic aryl or alkaryl acids containing 6-18 carbon atoms and 1 or 2 rings, e.g., benzoic, 2-, 3-, or 4-methylbenzoic, 2,3-, 2,4-, 2,5-, 2,6-, 3,4-, and 3,5-dimethylbenzoic, ethylbenzoic, 2,3,6-trimethylbenzoic, and 3-methyl-α-napthhoic acid; an aralkyl acid containing 7 to 18 carbon atoms, e.g., β-phenylpropionic; a polybasic acid containing 2-18 carbon atoms and 1 to 5 hydroxy groups, e.g., glycolic, lactic, citric, tartaric, d-maleic, d-glyceric and salicyclic acid; the corresponding acids containing one, two or more of simple substituents, e.g., halo, alkoxy, acyloxy, etc., in the molecule, e.g., chloroacetic, fluoroacetic, trichloroacetic, trifluoroacetic, 2,3,4-trimethoxybenzoic, phenoxyacetic, α-naphthoxyacetic acid, etc.

The acyl group of such equivalent compounds can also be that of sulfonic acid, e.g., an arylsulfonic, including benzenesulfonic, p-toluene-sulfonic, m,m'-dimethylbenzenesulfonic, o,o'-dimethylbenzenesulfonic, sym.-trimethylbenzenesulfonic, sym.-triethylbenzenesulfonic, m-ethylbenzenesulfonic, para-isopropylbenzenesulfonic, m-n-butylbenzenesulfonic acid, or an alkylsulfonic, e.g.,methanesulfonic, ethanesulfonic, propanesulfonic, isopropanesulfonic, butanesulfonic, tert.-butanesulfonic, pentanesulfonic, isopentanesulfonic, hexanesulfonic, heptanesulfonic, octylsulfonic or heterocyclic sulfonic, e.g, α-pyridinesulfonic α-pyranesulfonic, α-thiophensulfonic, α-furansulfonic, α-tetrahydrofuransulfonic, or other alkyl-, carbocyclic and heterocyclic aryl-, alkaryl- and aralkyl-sulfonic acid, preferably one containing 1-8 carbon atoms and 0-2, preferably 0-1 N, S or O heteroatoms, which are preferably ring carbon atoms in a heterocyclic ring.

The novel compounds of this invention are valuable as X-ray contrast media. Concentrated aqueous solutions of salts of these acids with inorganic or organic bases possess a low toxicity, a high excretory capability, predominantly via the urinary tract system and are of excellent compatibility intracerebrally and cerebrally. With respect to the cisternal compatibility, the novel compounds are superior to the conventional radiopaque agents. Aqueous solutions of the physiologically acceptable water-soluble salts can be used an injection preparations for uro-, angio- and myelography.

Preferred compounds of this invention are those compounds of Formula E which meet one or more of the following criteria:

a. Compounds in which A is divalent aminoloweralkanoyl derived from a naturally occurring amino acid, preferably a monoaminomonocarboxylic acid or a heterocyclic amino acid, e.g., histidine, tryptophan, proline, etc.;

b. Compounds in which A is an oligopeptide, preferably a dipeptide and especially when at least one of the peptide units is glycine, valine or leucine, c. Compounds in which R is alkyl, hydroxyalkyl or alkoxyalkyl of 1-3 carbon atoms, d. Compounds in which one of X and Y is hydroxy, especially thos in which X is hydroxy, e. Compounds in which one of $R_1$ and $R_2$ is hydrogen, alkyl of 1-6 carbon atoms or hydroxyalkyl of 2-6 carbon atoms, especially when the other of $R_1$ and $R_2$ is hydrogen, f. Compounds in which one of X and Y is morpholino, pyrrolidino, or piperazinc, especially when the other of X and Y is hydroxy Specific compounds of Formula I, in addition to those shown in the Examples, include N-(3-carboxy-5-methoxyacetamido-2.4.6.-triidobenzoyl)-DL-threonine Methylamide, N-(3-carboxy-5-methoxyacetamido-2.4.6-triiodobenzoyl) O-methyl-DL-serine Methylamide, N-(3-methylaminocarbonyl-5-acetamido-2.4.6-triiodobenzoyl)-O-methyl-DL-serine, N-(3-carboxy-5-methoxyacetamido-2.4.6.-triiodobenzoyl)-N-methyl-β-alanine Methylamide,
N-(3-carboxy-5-acetamido-2.4.6-triiodobenzoyl)-N-methyl-DL-alanine Methylamide,
N-(3-methylaminocarbonyl-5-acetamido-2.4.6-triiodobenzoyl)-N-cyclohexyl-β-alanine,
N-(3-aminocarbonyl-5-acetamido-2.4.6-triiodobenzoyl)-N-methyl Alanine,
N-(3methylaminocarbonyl-5-methoxyacetamido-2.4.6-triiodobenzoyl)-N-methyl-β-alanine,
N-(3-methylaminocarbonyl-5-acetamido-2.4.6-triiodobenzoyl)-DL-alanine,
N-(3-methylaminocarbonyl-5-hydrovacetamido-2.4.6-triiodobenzoyl)-γ-aminobutyric Acid,
N-(3-carboxy-5-acetamido-2.4.6-triiodobenzoyl)-γ-aminobutyric acid Amide,
N-(3-Methylaminocarbonyl-5-methoxyacetamido-2.4.6-triiodobenzoyl)-DL-phenyl-glycine,
N-(3-carbo xy-5-acetamido-2.4.6-triiodobenzoyl)-L-glutamic Acid-bis [methylamide]
N-(3-methylaminocarbonyl-5-methoxyacetamido-2.4.6-triiodobenzoyl)-DL-aspartic Acid,
N-(3-methylaminocarbonyl-5-acetamido-2.4.6-triiodobenzoyl)-DL-asparagine,
N-(3-methylaminocarbonyl-5-methoxyacetamido-2.4.6-triiodobenzoyl)-L-phenylalanine,
N-(3-methylaminocarbonyl-5-acetamido-2.4.6-triiodobenzoyl)-DL-α-aminobutyric Acid,
N-(3-carboxy-5-acetamido-2.4.6.-triiodobenzoyl)-ε-acetyl-L-lysine-amide,
N-(3-methylaminocarbonyl-5-acetamido- 2.4.6.-triiodobenzoyl)-α-acetyl-L-ornithine,
N-(3-ethanolaminocarbonyl-5-methoxyacetamido-2.4.6-triiodobenzoyl)-glycine,
N-(3-methylaminocarbonyl-5-acetamido-2.4.6-triiodobenzoyl)-L-proline,
N-(3-carboxy-5-methoxyacetamido-2.4.6-triiodobenzoyl)-L-leucine Methylamide,
N-(3-carboxy-5-acetamido-2.4.6-triiodobenzoyl)-O-methyl-L-tyrosine-Methylamide.

The following Table 1 lists the significant properties of illustrative compounds of this invention, denoted by A, B, C, D, E, F, G, in comparison with those of the structurally comparable, conventional substance H.

A: N-(3-carboxy-5-acetamido-2,4,5-triiodobenzoyl)-glycine amide.
B: N-(3-carboxy-5-acetamido-2,4,6-triiodobenzoyl)-DL-alanine methylamide.
C: N-(3-carboxy- 5-methoxyacetamido-2,4,6-triiodobenzoyl)-glycine methylamide.
D: N-(3-methylaminocarbonyl-5-acetamido-2,4,6-triiodobenzoyl)-sarcosine
E: N-(3-aminocarbonyl-5-acetamido-2,4,6-triiodobenzoyl)-glycine.
F: N-(3-carboxy-5-methoxyacetamido-2,4,6-triiodobenzoyl)-DL-serine methylamide.
G: N-(3-carboxy-5-hydroxyacetamido-2,4,6-triiodobenzoyl)-glycine methylamide.
H: "Iotalamat" = 3-acetamido-5-methylcarbamoyl-2,4,6-triiodobenzoic acid (U.S. Pat. No. 3,145,197).

All substances were tested as methylglucamine salts with 200 mg. I/ml. of solution. The intracerebral compatibility was determined on rats in accordance with Valzelli, Med. Exp. 11: 23–26 (1964).

In order to determine the cisternal compatibility, the test compounds were injected in varying doses (0.008 – 0.200 ml./kg.) by means of a Hamilton No. 710 syringe directly into the suboccipital cisterna of rats which were under a slight ether narcosis.

Cerebral compatibility was likewise determined on rats. In an operation under a slight ether narcosis, a catheter was affixed in the left common carotid artery; the distal end of the catheter, after having been passed through the lateral connective tissue of the neck, was fixed in the center of the back. Three hours late, the test compounds were cranially injected in varying doses (14.0 – 26.0 ml./kg.) into the artery.

As a measure of physiological compatibility, the $ED_{50}$ was determined in each case. i.e., the dose at which an undesired array of neurological symptoms (including convulsions and death) is evoked in 50% of the animals.

TABLE 1

| $ED_{50}$ in mg. I/kg. | (1) "Iotalamat" (H) | (2) Compounds A – G | |
|---|---|---|---|
| | MYELOGRAPHY | | ANGIOGRAPHY |
| Compound | Intracerebral Compatibility According to Valzelli | Cisternal Compatibility | Cerebral Compatibility |
| A | (1) 60.86 (2) 70.72 | (1) 10.56 (2) 11.17 | |
| B | (1) 61.92 (2) 66.30 | (1) 10.9 (2) 16.7 | |
| C | (1) 61.28 (2) 53.97 | (1) 10.07 (2) 20.04 | |
| D | (1) 59.83 (2) 76.21 | (1) 10.30 (2) 11.93 | (1) 3.38 (2) 3.99 |
| E | (1) 56.59 (2) 69.84 | (1) 10.56 (2) 14.42 | |
| F | (1) 59.83 (2) 81.32 | (1) 11.8 (2) 22.8 | (1) 4.20 (2) 3.78 |
| G | (1) 56.59 (2) 62.62 | (1) 9.8 (2) 11.8 | (1) 3.20 (2) 3.55 |

It can be seen from Table 1 that the compounds of this invention, especially with respect to their cisternal compatibility, are markedly superior to the conventional compound H.

The compounds of general Formula E of the present invention can be produced by reacting novel compounds of general Formula Z

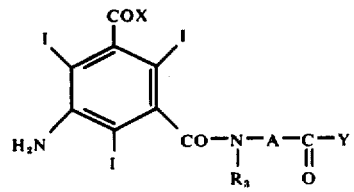

wherein A, X and Y have the above indicated values, with an amino acylating agent of the formula RCO—W, wherein R have the above-indicated value and W represents a carboxylic acid functional group, e.g., a carboxylic acid halide, an acid anhydride, or a carboxylic acid ester. Acylation is effected in the presence of catalytic amounts of a mineral acid, e.g., sulfuric acid or perchloric acid. Suitable acylation solvents are well known in the art and include but are not limited to excess acid anhydride, acid, acid esters or mixtures thereof. Preferred acylating agents are the carboxylic acid halides, preferably in a polar aprotic solvent, e.g., dimethylacetamide.

Compounds of general Formula E wherein X is

and Y is hydroxy can also be prepared by reacting compounds of the general Formula Z'

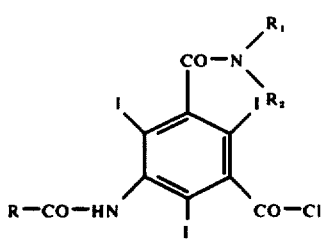

wherein R, $R_1$ and $R_2$ have the above-indicated values with amino acids in the presence of organic or inorganic bases or with amino acid esters, and optionally subsequently saponifying the thus obtained esters. The reaction with amino acids or amino acid esters is preferably conducted in a cyclic ether solvent, e.g., dioxane or tetrahydrofuran.

The compounds of general Formula Z' useful as a starting material are described in German Unexamined Published Application No. 2,031,724.

The compounds of general Formula Z, which represent a particularly important group of starting compounds, can be prepared in accordance with conventional processes.

For example, in order to prepare compounds of Formula Z wherein X is hydroxy group and Y is group

3-methoxycarbonyl-5-nitrobenzoyl chloride (J. Med. Chem. 6:24 (1963) is reacted with an amino acid amide to the corresponding N-(3-methoxycarbonyl-5-nitrobenzoyl)-amino acid amide (I). The latter is saponified to the acid II in a customary manner, converted into the aminoisophthalic acid monoamino acid amide (III) by reduction (hydrogenation at elevated pressure with Raney nickel as the catalyst), and this product can then be iodated, e.g., with $KICl_2$, to the desired compound IV.

The amino acid amides are obtained in a conventional manner by the reduction of amino acid alkyl esters with ammonia or with the corresponding amines.

The compounds of the general Formula Z wherein X is and Y is hydroxy can be produced, for example, by reacting 3-methoxycarbonyl-5-nitrobenzoyl chloride (J. Med. Chem. 6:24, 1963) with an amino acid to the corresponding N-(3-methoxycarbonyl-5-nitrobenzoyl)-amino acid (VI); thereafter amidating the methoxycarbonyl group to VII, with a correspondingly substituted amine or ammonia; hydrogenating the nitro group; and iodating the amino compound (VIII) to IX.

N-(3-methoxycarbonyl-5-nitrobenzoyl)-amino acid amide (I) can also be obtained by reacting the corresponding amino acid (VI) with an amine, e.g., in accordance with the method used to prepare mixed anhydrides.

The reactions will be explained in greater detail with reference to the following scheme of formulae:

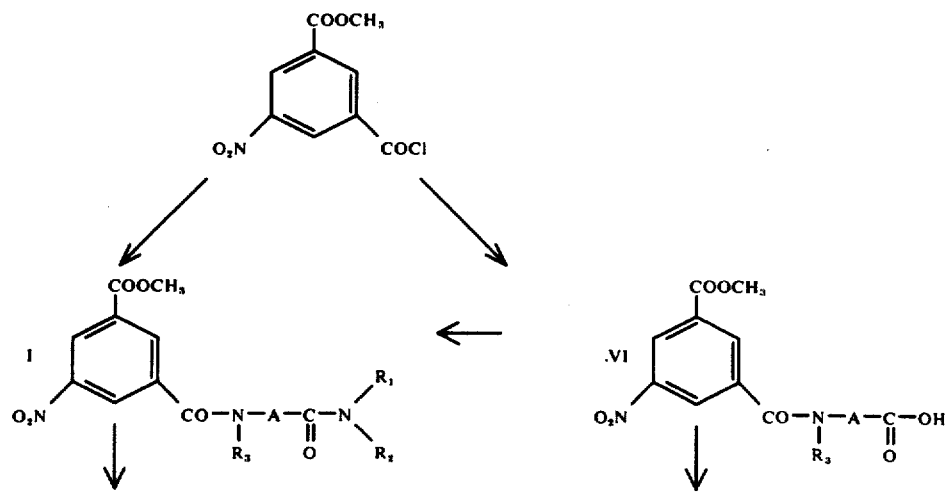

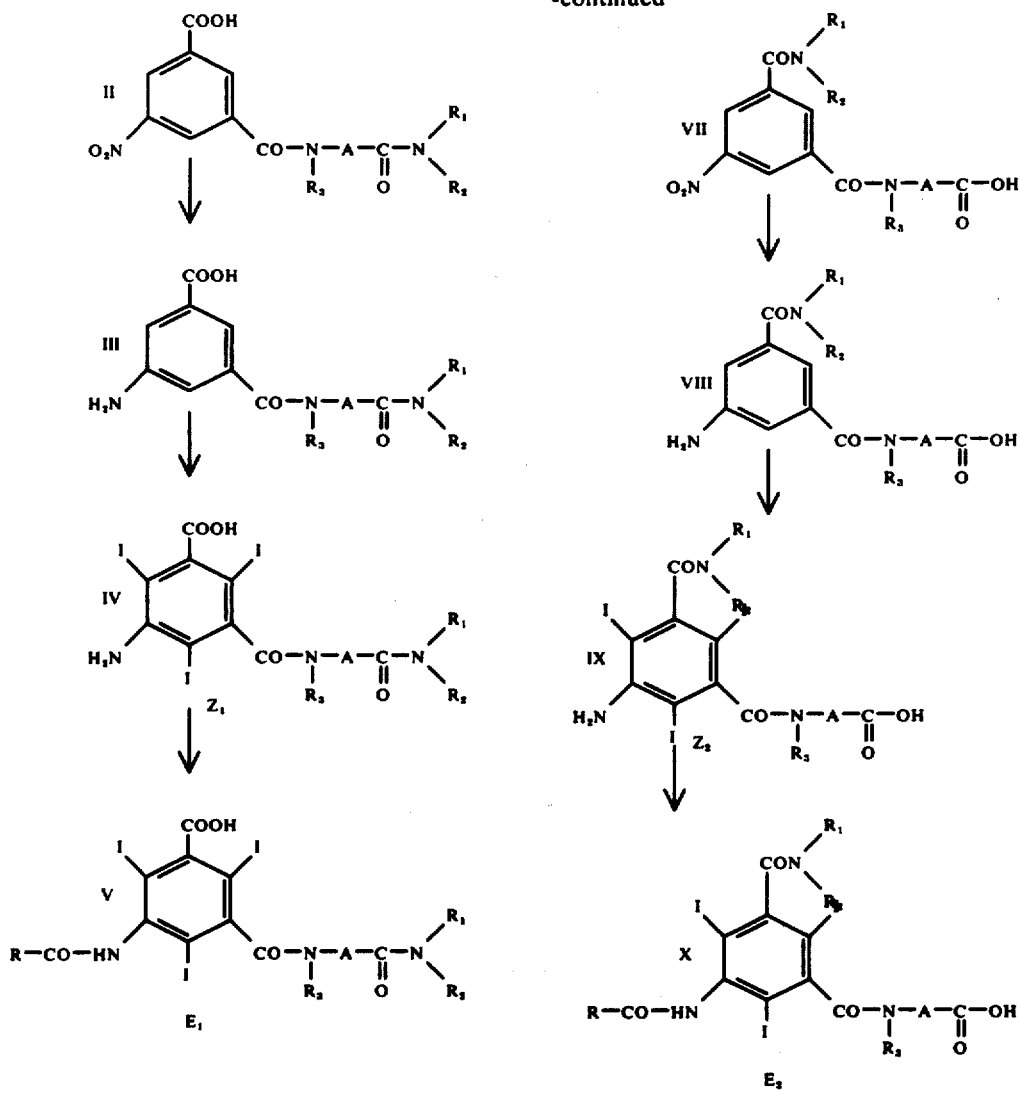

The novel iiodized isophthalic acid monoamino acid amides of Formula E are valuable contrast agents for radiopaque materials and novel intermediates for the production of radiological contrast substances.

One ore more of the compounds of this invention can be employed in mixture with conventional excipients, i.e., pharmaceutically acceptable organic or inorganic carrier substances suitable of parenteral application which do not deleteriously react with the active compounds. Suitable pharmaceutically acceptable carriers include but are not limited to water, salt solutions, etc.

For parenteral application, particularly suitable are solutions, preferably aqueous solutions. Ampoules are convenient unit dosages, or multivials containing multiple unit dosages can be used.

For intravenous administration the soluble salts of this invention are preferably used in aqueous solution whereby the concentration of the salts is preferably between about 15% by volume and about 75% by volume. Generally the amount of active agent per unit dosage is about 5 to 50 g., preferably 7 to 35 g.

The acids, in the form of their water-soluble physiologically compatible salts, are extraordinarily good radiopaque agents for myelography, urography, and angiography.

The salt solutions are characterized by a relatively low viscosity and can be administered by intravenous injection. The salt solutions are furthermore distinguished by a good circulatory compatibility and a low toxicity.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, the temperatures are set forth in degrees Celsius. Unless otherwise indicated, all parts and percentages are by weight.

The starting compounds can be prepared as follows:

N-(3-methoxycarbonyl-5-nitrobenzoyl)-glycine Methylamide (Ia)

Process 1:

Under ice cooling, 378.0 g. (4.5 moles) of sodium bicarbonate is added to 193.3 g. (1.55 moles) of glycine methylamide hydrochloride in 3.75 liters of water. Over a period of 3 hours, 365.4 g. of 3-methoxycarbonyl-5-nitrobenzoyl chloride in 1.3 l. of acetone is added dropwise to this reaction mixture. Thereafter, the mixture is stirred for 1½ hours at room temperature; the product is vacuumfiltered, washed free of salt with water, and dried under vacuum at 70° C.

Yield: 424 g. For purposes of analysis, the product is rcrystallized from methanol or acetonitrile. M.P. 174°–175° C.

Process 2:

8.5 g. (0.03 mole) of N-(3-methoxycarbonyl- 5-nitrobenzoyl)- glycine (VIa) dissolved in 130 ml. of absolute tetrahydrofuran, is cooled to −15° C., after the addition of 4.2 ml. of triethylamine, and mixed under agitation with 3 ml. of the ethyl ester of chlorocarbonic acid. The reaction mixture is agitated for about 10 minutes at −10° to −5° C., and a solution of 2.8 ml. of methylamine in 20 ml. of absolute tetrahydrofuran, cooled to −15° C., is gradually added thereto dropwise under agitation. Then, the mixture is stirred for another 30 minutes at −15° C. and subsequently overnight at room temperature; the triethylamine hydrochloride is filtered off, the filtrate concentrated under vacuum, and the residue recrystallized from acetonitrile; yield 4.6 g. m.p. 173°–174° C.

N-(3-carboxy-5-nitrobenzoyl)-glycine Methylamide (IIa)

443.0 g. (1.5 moles) of N-(3-methoxycarbonyl-5-nitrobenzoyl)-glycine methylamide in 5.5 l. of dioxane is agitated for 2 hours at room temperature with the addition of 3.3 l. of 0.5N sodium hydroxide solution. Thereafter, 400 ml. of water is added to the reaction mixture, the dioxane is distilled off under vacuum, and the acid is precipitated with concentrated hydrochloric acid, vacuum-filtered, washed free of salt with water, and dried under vacuum at 70° C.

Yield: 408 g. M.P. 256°–257° C.

N-(3-carboxy-5-aminobenzoyl)-glycine Methylamide (IIIa)

449.9 g. (1.6 moles) of N-(3-carboxy-5-nitrobenzoyl)glycine methylamide in 2 l. of water is dissolved with the addition of 880 ml. of 2N ammonia and hydrogenated at room temperature with 10% Raney nickel as the catalyst at about 120 atmospheres gauge. After separation of the catalyst, the remaining hydrogenation solution is further employed as such for iodation. The free compound can be obtained from the frothy ammonium salt, dissolved in methanol, by precipitation with trifluoroacetic acid.

Yield: 352 g. M.P. 236°–237° C.

N-(3-carboxy-5-amino-2,4,6-triiodobenzoyl)-glycine Methylamide (IVa)

A solution of the ammonium salt of N-(3-carboxy-5-aminobenzyl)-glycine methylamide, produced by hydrogenation of 1.6 moles of the corresponding nitro compound, is replenished with water to 140 liters and, under agitation, 3.6 l. of concentrated hydrochloric acid and 3.5 l. of 2N KICl$_2$ solution are added thereto. After three days of agitation, the reaction product is filtered from the precipitate, thoroughly washed with water, then agitated for 2 hours with water, vacuum-filtered, and dried under vacuum at 70° C.

Yield: 910.5 g. M.P. 252°–253° C (under decomposition).

N-(3-methoxycarbonyl-5-nitrobenzoyl)-glycine (VIa)

Under agitation and during the course of 2½ hours, 183.0 g. (0.75 mole) of 3-methoxycarbonyl-5-nitrobenzoyl chloride in 750 ml. of acetone is added dropwise to a solution of 62.0 g. (0.825 mole) of glycine and 189.0 G. of sodium bicarbonate in 3 l. of water. The first-obtained precipitate is gradually dissolved again after an additional three hours of agitation. Thereafter, the reaction mixture is extracted twice with ether, the aqueous phase is acidified with concentrated hydrochloric acid, the thus-precipitated oil is extracted repeatedly with ethyl acetate, and the combined ethyl acetate extracts, after washing with water and drying with sodium sulfate, are mixed with a stoichiometric amount of dicyclohexylamine. After allowing the reaction mixture to stand for some time, it is filtered off from the precipitated dicyclohexylammonium salt (m.p. 204°–205° C. form chloroform/ether), washed several times with ether, and the acid is liberated again by distributing the reaction mixture between ethyl acetate and 2N sulfuric acid. After washing the ethyl phases with water, drying with sodium sulfate, and concentrating under vacuum, 181.0 g. of the above-identified compound is obtained. M.P. 142°–143° C.

N-(3-methylaminocarbonyl-5-nitrobenzoyl)-glycine Methylammonium Salt (VIIa)

15 ml. of liquid methylamine is added at 0° C. to 42.3 g. (0.15 mole) of N-(3-methoxycarbonyl-5-nitrobenzoyl)-glycine (VIa) in 150 ml. of methanol; the reaction mixture is stored for 3 days at room temperature. Then, the mixture is concentrated to dryness under vacuum, and the residue is refluxed with absolute alcohol. After cooling, the reaction mixture is filtered, washed with alcohol and dried under vacuum.

Yield: 43.2 g. M.P. 216°–217° C.

N-(3-Methylaminocarbonyl-5-aminotriiodobenzoyl)-glycine (IXa)

43.7 g. (0.14 mole) of N-(3-methylaminocarbonyl-5-nitrobenzoyl)-glycine methylammonium salt (VIIa) in 0.6 l. of water is hydrogenated, with Raney nickel as the catalyst, at about 140 atm. gauge and at room temperature. After removel of the catalyst, 15.4 l. of water, 280 ml. of concentrated hydrochloric acid, and 280 ml. of 2N KICl$_2$ solution are added to the filtrate, and the mixture is stirred for 48 hours at room temperature. Then, the mixture is filtered off from the precipitate, thoroughly washed with water, the product is agitated for some time with water, and dried at 70° C. under vacuum.

Yield: 74.2 g. M.P. 265°–266° C (under decomposition).

In an analogous manner, the other starting compounds are likewise produced. Table 4 indicates the yields and melting points of several compounds I through IV and VI through IX.

See Tables, next two pages.

TABLE 2

| N—A—C<br>\|  \|\|<br>R$_3$ O | R$_1$ | R$_2$ | I<br>% Yield | M.P. °C | II<br>% Yield | M.P. °C | M.P. °C | III<br>% Yield | IV<br>M.P. °C.(Z) |
|---|---|---|---|---|---|---|---|---|---|
| a) Gly | H | CH$_3$ | 96 | 174–175 | 97 | 256–257 | 236–237 | 90 | 252–253 |

TABLE 2-continued

| N—A—C \| \|\| R₃  O | R₁ | R₂ | I % Yield | I M.P. °C. | II % Yield | II M.P. °C. | III M.P. °C. | IV % Yield | IV M.P. °C.(Z) |
|---|---|---|---|---|---|---|---|---|---|
| b) DL-Ser | H | CH₃ | 71 | 169–170 | 82 | 239–240 | 223–224 | 78 | 259–260 |
| c) Gly | H | H | 86 | 190–191 | 90 | 245–246 | 231–233 | 51 | 248–249 |
| d) DL-Ala | H | CH₃ | 62 | 173–174 | 97 | 248–250 | 217–219 | 73 | 208–209 |
| e) Sar | H | CH₃ | 91 | 126–127 | 85 | 212–213 | Foam | 92 | 238–240 |
| f) β-Ala | H | CH₃ | 81 | 181–182 | 90 | 247–248 | 199–200 | 80 | 170/250–252 |
| g) L-Phe | H | CH₃ | 90 | 204–205 | 99 | 238–239 | 235–237 | 93 | 281–282 |
| h) L-Pro | H | CH₃ | 77 | 159–160 | 89 | 228–229 | * | 84 | 248–250 |
| i) GlyGly | H | CH₃ | 89 | 219–220 | 93 | 249–250 | 244–245 | 52 | 230–232 |
| k) Gly-L-Leu | H | CH₃ | 79 | 191–192 | 98 | 223–225 | * | 36 | 228–230 |
| l) Gly | | ⟨O⟩ | 36 | 194–195 | 68 | 227–228 | * | 73 | ~200 |
| m) Gly | H | CH₂CH₂OH | 47 | 171–172 | 99 | 191–192 | * | 79 | 201–202 |
| n) Gly | CH₃ | CH₃ | 63 | 174–175 | 94 | 236–237 | * | 62 | 239–241 |
| o) DL-Abu | H | CH₃ | 70 | 215–216 | 92 | 254–256 | * | 79 | ~220 |
| p) DL-Val | H | CH₃ | 73 | 235–236 | 98 | 249–251 | * | 84 | ~235 |
| r) L-Val-L-Val | H | CH₃ | 30 | 308–310 | 90 | 292–293 | * | 87 | 247–248 |
| s) N-phenyl-β-Ala | H | CH₃ | 77 | 110–112 | 96 | 205–207 | * | 85 | 220 |

*Substance processed further without isolation.

TABLE 3

| N—A—C \| \|\| R₃  O | VI % Yield | VI M.P. °C. | R₁ | R₂ | VII % Yield | VII M.P. °C. | VIII M.P. °C. | IX % Yield | IX M.P. °C.(Z) |
|---|---|---|---|---|---|---|---|---|---|
| a) Gly | 85 | 142–143 | H | CH₃ | 92 | 216–217 | * | 84 | 265–266 |
| b) Gly | | | H | H | 100 | 245–246 | * | 80 | 271–272 |
| c) β-Ala | 69 | 168–169 | H | CH₃ | 89 | 185–186 | * | ~76 | 190 |
| d) β-Ala | | | H | H | 62 | 202–203** | * | 81 | 239–241 |
| e) DL-Ser | 61 | 174–175 | H | CH₃ | 95 | 180–182** | * | 70 | 247–248 |
| f) DL-thr | 64 | 168–169 | H | CH₃ | 69 | 190–192** | * | 95 | 263–264 |
| g) Sar | 80 | 135–136 | H | CH₃ | 97 | 188–189 | * | 69 | 236–237 |
| h) Gly-Gly | 93 | 193–194 | H | CH₃ | 70 | 205–207 | * | 77 | 245–246 |

*Substance processed further without isolation.
**As the methylammonium and/or ammonium salt.

EXAMPLE 1

N-(3-Carboxy-5-acetamido-2,4,6-triiodobenzoyl)-glycine Methylamide a. 629.0 g. (1 mole) of N-(3-carboxy-5-amino-2,4,6-triiodobenzoyl)-glycine methylamide (IVa), m.p. 252°–253° C. (decomposition), is dissolved in 1.2 l. of dimethylacetamide and, under cooling and agitation, 170 ml. of acetyl chloride is added dropwise thereto. The reaction mixture is stirred overnight at room temperature, some water is added, and the mixture is concentrated under vacuum. The remaining oil is treated under agitation with 600 ml. of water, thus obtaining a solid precipitate. The product is allowed to stand for some time, the compound is vacuum-filtered, washed thoroughly with water, and then dissolved in 2.5 l. of water with the addition of the stoichiometric amount of 2N ammonia. The solution is treated for 2 hours with activated carbon and finally, after removal of the carbon, the filtrate is acidifed with concentrated hydrochloric acid. After allowing the reaction mixture to stand overnight, the product is vacuuum-filtered, washed with water, then stirred with water for a certain period of time, again filtered, and dried under vacuum at 70° C.

Yield: 611 g. (91%), m.p. 284°–285° C. (under decomposition).

Analysis: $C_{13}H_{12}I_3N_3O_5$ (671.0). Calculated: C 23.27%, H 1.80%, I 56.74%, N 6.26%, E 671. Found: 23.53, 1.78, 56.69, 6.35, 668.

b. The above-mentioned compound can also be obtained in a conventional manner by acetylation with acetic anhydride in glacial acetic acid in the presence of concentrated sulfuric acid as the catalyst, with a yield of 52%, m.p. 282°–283° C. (under decomposition).

EXAMPLE 2

N-(3-Carboxy-5-acetamido-2,4,6-triiodobenzoyl)-DL-serine Methylamide 82.4 g. (0.125 mole) of N-(3-carboxy-5-amino-2,4,6-triiodobenzoyl)-DL-serine methylamide (IVb) m.p. 259°–260° C. (decomposition), is dissolved in 200 ml. of dimethylacetamide; under agitation, 33.4 ml. of acetyl chloride is added dropwise thereto. The reaction mixture is agitated for 20 hours, mixed with 40 ml. of water, and, after another 30 minutes of agitation, concentrated under vacuum. The residue is stirred overnight with 150 ml. of water, the precipitate is vacuum-filtered, stirred in 150 ml. of 1N sodium hydroxide solution with the addition of 15 ml. of 37% strength sodium hydroxide solution and activated carbon for 2 hours, the activated carbon is removed, and the filtrate is brought to pH 1 with concentrated hydrochloric acid. After allowing the reaction mixture to stand overnight at 0° C., the precipitate is vacuum-filtered, washed with ice water, and dried under vacuum at 70° C.

Yield: 62.0 g., m.p. 276°–277° C. (under decomposition).

Analysis: $C_{14}H_{14}I_3N_3O_6$ (701.0). Calculated: C 23.99%, H 2.01%, I 54.31%, E 701.0. Found: 24.30, 2.40, 54.27, 696.0.

EXAMPLE 3

N-(3-Carboxy-5-acetamido-2,4,6-triiodobenzoyl)-glycine Amide

Under agitation and cooling with wter, 13.5 ml. of acetyl chloride is added dropwise to 40.0 g. (65 millimoles) of N-(3-carboxy-5-amino-2,4,6-triiodobenzoyl)-glycine amide IVc), m.p. 248°–249° C. (decomposition), in 80 ml. of dimethylacetamide. Then, the reaction mixture is stirred at at room temperature for 1½ hours, another 2 ml. of acetyl chloride is added thereto, and the mixture stirred for another hour. After the addition of 10 ml. of water, the reaction mixture is concentrated under vacuum, 70 ml. of water is added to the residue, and the mixture is stirred for 16 hours. The precipitate is vacuum-filtered and washed free of salt with water.

Yield: 40.0 g. (93.7%), m.p. 273°–274° C. (under decomposition).

Analysis: $C_{12}H_{10}I_3N_3O_5$ (657.0). Calculated: C 21.93%, H 1.54%, N 6.39%, I 57.95%, E 657. Found: 21.87, 2.08, 5.89, 57.80, 650.

EXAMPLE 4

N-(3-Carboxy-5-acetamido-2,4,6-triiodobenzyl)-DL-analine Methylamide

Analogously to Example 1, 95.2 g. (81.8%) of N-(3-carboxy-5-acetamido-2,4,6-triiodobenzoyl)-DL-alanine methylamide is obtained from 190.3 g. (0.17 mole) of N-(3-carboxy-5-amino-2,4,6-triiodobenzoyl)-DL-alanine methylamide (IVd), m.p. 208°–209° C. (decomposition), in 210 ml. of dimethylacetamide and 61.2 ml. of acetyl chloride. The melting point of the product is 273°–274° C. (under decomposition).

Analysis: $C_{14}H_{14}I_3N_3O_5$ (685.0). Calculated: C 24.53%, H 2.06%, N 6.13%, I 55.58%, E 685. Found: 24.70, 2.44, 6.14, 55.58, 689.

EXAMPLE 5

N-(3-Carboxy-5-acetamido-2,4,6-triiodobenzyl)-sarcosine Methylamide

Analogously to Example 3, 71.5 g. (74.5%) of N-(3-carboxy-5acetamido-2,4,6-triiodobenzoyl)-sarcosine methylamide, m.p. 270°–271° C. (under decomposition) is obtained from 90 g. (0.14 mole) of N-(3-carboxy-5-amino-2,4,6-triiodobenzoyl)-sarcosine methylamide (IVe), m.p. 238°–240° C. (decomposition) in 170 ml. of dimethylacetamide and 27.4 ml. of acetyl chloride.

Analysis: $C_{14}H_{14}I_3N_3O_5$ (685.0). Calculated: I 55.58%, E 685. Found: 55.54, 678.

EXAMPLE 6

N-(3-Carboxy-5-acetamido-2,4,6-triiodobenzoyl)-β-alanine Methylamide 99.5 g. (0.15 mole) of N-(3-carboxy-5-amino-2,4,6-triiodobenzoyl)-β-alanine methylamide · 1.1 $H_2O$ (IVf), m.p. 250°–252° C. (decomposition) in 190 ml. of dimethylacetamide yield, after reaction with 40.0 ml. of acetyl chloride analogously to Example 1, 60.4 g. (58.8%) of the desired compound. A sample for analysis is purified in alcohol by way of the dimethylammonium salt; m.p. 288°–289° C. (under decomposition).

Analysis: $C_{14}H_{14}I_3N_3O_5$ (685.0). Calculated: I 55.58%, E 685. Found: 55.58, 695.

EXAMPLE 7

N-(3-Carboxy-5-acetamido-2,4,6-triiodobenzoyl)-L-phenylalanine Methylamide

Analogously to Example 1, 67.5 g. (88.7%) of the desired compound, m.p. 276°–277° C. (under decomposition) is obtained from 71.9 g. (0.1 mole) of N-(3-carboxy-5-amino-2,4,6-triiodobenzoyl)-L-phenylalanine methylamide (IVg), m.p. 281°–282° C.. (decomposition), in 120 ml. of dimethylacetamide with 17 ml. of acetyl chloride.

Analysis: $C_{20}H_{18}I_3N_3O_5$ (761.1). Calculated: C 31.56%, H 2.38%, N 5.52%, I 50.0%, E 761. Found: 31.47, 2.55, 5.53, 50.0, 764.

EXAMPLE 8

N-(3-Carboxy-5-acetamido-2,4,6-triiodobenzoyl)-L-proline Methylamide

In accordance with Example 1, 36.5 g. (64%) of the desired compound, m.p. 245°–247° C. (under decomposition), is produced from 53.5 g. (0.080 mole) of N-(3-carboxy-5-amino-2,4,6-triiodobenzoyl)-L-proline methylamide (IVh) in 96 ml. of dimethylacetamide with 13.6 ml. of acetyl chloride.

Analysis: $C_{16}H_{16}I_3N_3O_5$ (711.1). Calculated: I 53.55%, E 711. Found: 53.64, 710.

EXAMPLE 9

N-(3-Carboxy-5-acetamido-2,4,6,-triiodo-benzoyl)-glycylcine Methylamide

From N-(3-carboxy-5-amino-2,4,6-triiodobenzoyl)-glycylglycine methylamide (IVi), m.p. 230°–232° C. (decomposition), in dimethylacetamide, 34.3% of the desired compound, m.p. 253°–255° C. (under decomposition) is obtained with the addition of acetyl chloride, as described in Example 1, and after recrystallization from aqueous acetonitrile.

Analysis: $C_{15}H_{15}I_3N_4O_6$ (728.1). Calculated: N 7.70%, I 52.3%. Found: 7.68, 52.1.

EXAMPLE 10

N-(3-Carboxy-5-acetamido-2,4,6-triiodobenzoyl)-glycyl-L-leucine Methylamide

Analogously to Example 1, the desired compound is produced from the corresponding 5-amino compound (IVk), m.p. 228°–230° C. (decomposition).

EXAMPLE 11

N-(3-Carboxy-5-methoxyacetamido-2,4,6-triiodobenzoyl)-glycine Methylamide

At maximally 10° C., 29.0 ml. of thionyl chloride is added dropwise under agitation to 28.2 ml. of methoxyacetic acid in 100 ml. of dimethylacetamide within 40 minutes. After, at 0° C., the reaction mixture has been agitated for another 2 hours, 63.0 g. (0.1 mole) of N-(3-carboxy-5-amino-2,4,6-triiodobenzoyl)-glycine methylamide (IVa), m.p. 252°–253° C. (decomposition), in 100 ml. of dimethylacetamide is added dropwise under agitation to the reaction mixture at maximally 8° C. during the course of one hour. Then, the solution is agitated overnight. After the addition of 5 ml. of water, the mixture is concentrated under vacuum, the residue is stirred with 700 ml. of water, the precipitate is vacuum-filtered, carefully washed with water, and, while still moist, reprecipitated from dilute ammonia with concentrated hydrochloric acid. After allowing the mixture to stand for some time, the acid is vacuum-filtered, washed well with water, stirred with fresh water, and, after another filtering step, dried under vacuum at 70° C.

Yield: 54.0 g. (77%) of a product which is uniform as determined by thin-layer chromatography and has a melting point of 226°–228° C. (under decomposition).

Analysis: $C_{14}H_{14}I_3N_3O_6$ (701.0). Calculated: I 54.3%, E 701. Found: 54.3, 706.

EXAMPLE 12

N-(3-Carboxy-5-methoxyacetamido-2,4,6-triiodobenzoyl)-L-phenylalanine Methylamide Analogously to Example 11, 51.5 g. (65%) of the desired substance, m.p. 250°–252° C. (under decomposition), is obtained from 71.9 g. (0.1 mole) of N-(3-carboxy-5-amino-2,4,6-triiodobenzoyl)L-phenylalanine methylamide (IV g), m.p. 281°–282° C.

Analysis: $C_{21}H_{20}I_3N_3O_6$ (791.1). Calculated: I 48.12 %, E 791. Found: 48.02, 796.

EXAMPLE 13

N-(3-Carboxy-5-valeroylamino-2,4,6-triiodobenzoyl)-glycine Methylamide

Under agitation and water cooling, 31.5 ml. of valeroyl chloride is added dropwise to 45.8 g. (0.073 mole) of N-(3-carboxy-5-amino-2,4,6-triiodobenzoyl)-glycine methylamide (IV a), m.p. 252°–253° C. (under decomposition), in 120 ml. of dimethylacetamide. After agitating the reaction mixture overnight at room temperature, the product is precipitated by adding water; then, the product is vacuum-filtered and purified by dissolving the corresponding sodium salt and separation of the free acid by the addition of a mineral acid.

Yield: 41.8 g. (80.1%), m.p. 258°–260° C. (under decomposition).

Analysis: $C_{16}H_{18}I_3N_3O_5$ (713.1). Calculated: I 53.4%, E 713. Found: 53.1, 706.

EXAMPLE 14

N-(3-Methylaminocarbonyl-5-acetamido-2,4,6-triiodobenzoyl)glycine

Under agitation, 20 ml. of acetyl chloride is added dropwise to 66.0 g. (0.105 mole) of N-(3-methylaminocarbonyl-5-amino-2,4,6-triiodobenzoyl)-glycine (IX a), m.p. 265°–266° C., in 140 ml. of dimethylacetamide, and the mixture is stirred overnight. After the addition of a small amount of water, the mixture is agitated for another 2 hours, concentrated under vacuum, and the oily residue is stirred with 50 ml. of water for 16 hours. Then, the precipitate is vacuum-filtered, washed with water, the compound is dissolved with 2N NH₄OH to form a neutral solution, treated with activated carbon, and, after the removal of the carbon, acidified with concentrated hydrochloric acid. After allowing the reaction mixture to stand for about 20 hours at room temperature, it is filtered, washed free of salt with water, and dried under vacuum at 70° C.

Yield: 45.6 g. (64.7%), m.p. 289°–291° C. (under decomposition).

Analysis: $C_{13}H_{12}N_3I_3O_5$ (671.0). Calculated: I 56.74%, E 671. Found: 56.66, 671.

Analogously, N-(3-methylaminocarbonyl-5-propionylamido-2,4,6-triiodobenzoyl)-glycine is prepared with propionyl chloride. This product has a melting point of 284°–286° C. (under decomposition).

EXAMPLE 15

N-(3-Methylaminocarbonyl-5-acetamido-2,4,6-triiodobenzoyl)-β-alanine 28.7

From 100.0 g. (0.155 mole) of N-(3-methylaminocarbonyl-5-amino-2,4,6-triiodobenzoyl)-β-alanine (IX c), m.p. about 190° C., in 190 ml. of dimethylacetamide, 70.1 g. (66.0%) of the above product, m.p. 295°–297° C. (under decomposition) is obtained with the addition of 18.7 ml. of acetyl chloride analogously to Example 14 and after reprecipitation from aqueous ammonia with hydrochloric acid.

Analysis: $C_{14}H_{14}I_3N_3O_5$ (685.0). Calculated: I 55.58%, E 685. Found: 55.56, 681.

EXAMPLE 16

(a) Methyl Ester of N-(3-Methylaminocarbonyl-5-acetamido-2,4,6-triiodobenzoyl)-glycine 0.1 mole of 3-methylaminocarbonyl-5-acetamido-2,4,6-triiodobenzoyl chloride (compound of general Formula Z' with $R_1 = H$, $R_2 = R_3 = CH_3$) and 0.2 mole of glycine methyl ester hydrochloride are heated in 700 ml. of dioxane, with the addition of 0.3 mole of triethylamine, for 4 hours to 60° C., and then agitated at room temperature for 15 hours. The product is filtered off from the precipitate, washed with water, and dried at 60° C. under vacuum, thus obtaining 47.3 g. (69%) of the desired compound having a melting point of 309°–311° C. (under decomposition).

Analysis: $C_{14}H_{14}I_3N_3O_5$ (685.0). Calculated: C 24.55%, H 2.06%, I 55.58%, N 6.13%. Found: 24.27, 2.18, 55.47,, 6.00.

(b) N-(3-Methylaminocarbonyl-5-acetamido-2,4,6-triiodobenzoyl)-glycine

The methyl ester obtained according to (a) is refluxed for 2 hours in alcohol, adding an excess of 1N sodium hydroxide solution; the product is precipitated with concentrated hydrochloric acid.

Yield: 65%, m.p. 288°–290° C. (under decomposition).

The substance is identical to the compound according to Example 14, as determined by thin-layer chromatography and IR spectrum.

EXAMPLE 17

N-(3-Carboxy-5-acetamido-2,4,6-triiodobenzoyl)-glycine Morpholide

The compound is obtained analogously to Example 1 by acetylation of N-(3-carboxy-5-amino-2,4,6-triiodobenzoyl)-glycine morpholide (IV l), m.p. about 200° C. (under decomposition), in dimethylacetamide.

Yield: 56%, m.p. 278°–279° C. (under decomposition).

Analysis: $C_{16}H_{16}I_3N_3O_6$ (727.0). Calculated: C 26.43%, H 2.22%, I 52.37%, N 5.78%, E 727. Found: 26.59, 2.31, 52.21, 5.97, 716.

EXAMPLE 18

N(3-Carboxy-5-acetamido-2,4,6-triiodobenzoyl)-glycine Ethanolamide

This compound is prepared analogously to Example 1 from N-3-carboxy-5-amino-2,4,6-triiodobenzoyl)-glycine ethanolamide (IV m), m.p. 201°–202° C.

(under decomposition). After concentrating the dimethylacetamide solution under vacuum, the residue is stored with saturated soda solution for 48 hours at room temperature, the acid is precipitated with concentrated hydrochloric acid, and once again purified by reprecipitation from aqueous ammonia with a mineral acid.

Yield: 59%, m.p. 271°–272° C. (under decomposition).

Analysis: $C_{14}H_{14}I_3N_3O_6$ (701.0). Calculated: C 23.99%, H 2.01%, I 54.31%, N 5.99%, E 701. Found: 24.09, 2.06, 54.04, 5.99, 696.

EXAMPLE 19

N-(3-Carboxy-5-acetamido-2,4,6-triiodobenzoyl)-glycine Dimethylamide

Analogously to Example 1, N-(3-carboxy-5-amino-2,4,6-triiodobenzoyl)-glycine dimethylamide (IV n), m.p. 239°–241° C. (under decomposition) is acetylated with acetyl chloride in dimethylacetamide.

Yield: 62%, m.p. 251°–253° C. (under decomposition).

Analysis: $C_{14}H_{14}I_3N_3O_5$ (685.0). Calculated: C 24.55%, H 2.06%, I 55.58%, N 6.13%, E 685. Found: 24.38, 2.44, 55.52, 6.06, 677.

EXAMPLE 20

N-(3-Methylaminocarbonyl-5-acetamido-2,4,6-triiodobenzoyl)-sarcosine

The compound is obtained in accordance with Example 14 from N-(3-methylaminocarbonyl-5-amino-2,4,6-triiodobenzoyl)-sarcosine (IX g), m.p. 228°–229° C. (under decomposition), and acetyl chloride in dimethylacetamide; this product has a melting point of 287°–289° C. (under decomposition).

Analysis: $C_{14}H_{14}I_3N_3O_5$ (685.0).
Calculated: I 55.58%, E 685.
Found: 55.28, 675.

EXAMPLE 21

N-(3-Aminocarbonyl-5-acetamido-2,4,6-triiodobenzoyl)-glycine

This compound is produced analogously to Example 14 from 61.5 g. (0.1 mole) of N-(3-aminocarbonyl-5-amino-2,4,6-triiodobenzoyl)-glycine (IX b), m.p. 271°–272° C. (under decomposition), in 120 ml. of dimethylacetamide and 22 ml. of acetyl chloride.

Yield: 54.8 g. (83.4%), m.p. about 310° C. (under decomposition).

Analysis: $C_{12}H_{10}I_3N_3O_5$ (657.0).
Calculated: C 21.93%, H 1.54%, I 57.95%, N 6.39%, E 657.
Found: 22.21, 1.71, 57.71, 6.47, 656.

EXAMPLE 22

N-(3-Carboxy-5-methoxyacetamido-2,4,6-triiodobenzoyl)-DL-serine Methylamide

According to Example 11, the above compound is obtained from N-(3-carboxy-5-amino-2,4,6-triiodobenzoyl)-DL-serine methylamide (IV b), m.p. 259°–260° C. (under decomposition) and methoxyacetic acid/thionyl chloride in dimethylacetamide.

Yield: 72%, m.p. 270°–272° C. (under decomposition).

Analysis: $C_{15}H_{16}I_3N_3O_7$ (731.0).

Calculated: C 24.64%, H 2.21%, I 52.08%, N 5.75%, E 731.
Found: 24.90, 2.36, 52.07, 5.93, 726.

EXAMPLE 23

N-(3-Carboxy-5-hydroxyacetamido-2,4,6-triiodobenzoyl)-glycine Methylamide

At temperatures of maximally 10° C., 44 ml. of acetoxyacetyl chloride is gradually added dropwise under agitation to a solution of 63 g. (0.1 mole) of N-(3-carboxy-5-amino-2,4,6-triiodobenzoyl)-glycine methylamide (IV a), m.p. 252°–253° C. (under decomposition) in 100 ml. of dimethylacetamide. After 8 hours of agitation at room temperature, 500 ml. of water is added to the reaction mixture, the thus-precipitated product is filtered off, after allowing the mixture to stand for some time at 0° C., thoroughly washed, and dissolved in 150 ml. of 2N sodium hydroxide solution and 500 ml. of water. The solution is heated for 1 hour on a steam bath under agitation. After cooling, another 500 ml. of water is added, and the product is precipitated with concentrated hydrochloric acid. After vacuum-filtering, thorough washing, and drying under vacuum, 51 g. (74.2%) of a crude product is obtained. For further purification, the ammonium salt, isolated from methanol, is converted in an aqueous solution with concentrated hydrochloric acid, into the free acid, m.p. 227°–229° C. (under decomposition).

Analysis: $C_{13}H_{12}I_3N_3O_6$ (687.0).
Calculated: C 22.73%, H 1.76%, I 55.42%, N 6.12%, E 687.
Found: 22.98, 1.76, 55.09, 6.22, 698.

EXAMPLE 24

N-(3-Methylaminocarbonyl-5-acetamido-2,4,6-triiodobenzoyl)-DL-threonine

This compound is produced analogously to Example 2 from N-(3-methylaminocarbonyl-5-amino-2,4,6-triiodobenzoyl)-DL-threonine (IX f), m.p. 263°–264° C. (under decomposition) and acetyl chloride in dimethylacetamide.

Yield: 58.1%, m.p. 264°–265° C. (under decomposition).

Analysis: $C_{15}H_{16}I_3N_3O_6$ (715.0).
Calculated: C 24.19%, H 2.26%, I 53.24%, N 5.88%, E 715.
Found 24.29, 2.39, 53.25, 5.77, 713.

EXAMPLE 25

N-(3-Aminocarbonyl-5-acetamido-2,4,6-triiodobenzoyl)-β-alanine

This compound, m.p. 277°–279° C. (under decomposition) is produced analogously to Example 2 from the corresponding triiodoamino compound (IX d), m.p. 239°–241° C. (under decomposition), and acetyl chloride in dimethylacetamide.

Analysis: $C_{13}H_{12}I_3N_3O_5$ (671.0).
Calculated: C 23.27%, H 1.80%, I 56.74%, N 6.26% E 671.
Found: 23.07, 2.10, 56.79, 6.29, 672.

EXAMPLE 26

N-(3-Methylaminocarbonyl-5-acetamido-2,4,6-triiodobenzoyl)-DL-serine

This compound is produced analogously to Example 2 by acetylation of the 5-amino compound (IX e), m.p.

247°–248° C. (under decomposition), with acetyl chloride in dimethylacetamide.

Yield: 75.4%, m.p. 257°–259° C. (under decomposition).

Analysis: $C_{14}H_{14}I_3N_3O_6$ (701.0).

Calculated: C 23.99%, H 2.01%, I 54.31%, N 6.00%. Found 23.68, 2.32, 54.64, 6.13.

EXAMPLE 27

N-(3-Carboxy-5-methoxyacetamido-2,4,6-triiodobenzoyl)-LD-alanine Methylamide

This compound is obtained as described in Example 11 from N-(3-carboxy-5-amino-2,4,6-triiodobenzoyl)-DL-alanine methylamide (IV d), m.p. 208°–209° C. (under decomposition), and methoxyacetyl chloride.

Yield: 71%, m.p. 239°–241° C. (under decomposition).

Analysis: $C_{15}H_{16}I_3N_3O_6$ (715.0).

Calculated: C 25.19%, H 2.26%, N 5.88%, I 53.24%, E 715.

Found: 24.70, 2.63, 5.69, 53.51, 712.

EXAMPLE 28

N-(3-Carboxy-5-acetamido-2,4,6-triiodobenzoyl)-DL-α-aminobutyric Acid Methylamide Analogously to Example 1, this compound is produced from N-(3-carboxy-5-amino-2,4,6-triiodobenzoyl)-DL-α-aminobutyric acid methylamide (IV o), m.p. about 220° C. (under decomposition), and acetyl chloride.

Yield: 59%, m.p. 249°–251° C. (under decomposition).

Analysis: $C_{15}H_{16}I_3N_3O_5$ (699.0). Calculated: N 6.01%, I 54.46%, E 699. Found: 5.99, 54.13, 698.

EXAMPLE 29

N-(3-Carboxy-5-methoxyacetamido-2,4,6-triiodobenzoyl)-DL-α-aminobutyric Acid Methylamide This compound is produced analogously to Example 11 by reacting N-(3-carboxy-5-amino-2,4,6-triiodobenzoyl)-DL-α-aminobutyric acid methylamide (IV o), m.p. about 220° C. (under decomposition), with methoxyacetic acid/thionyl chloride.

Yield: 55%, m.p. 270°–272° C. (under decomposition).

Analysis: $C_{16}H_{18}I_3N_3O_6$ (729.0).

Calculated: C 26.36%, H 2.49%, N 5.76%, I 52.22%, E 729.

Found 26.52, 2.75, 6.00, 51.64, 733.

EXAMPLE 30

N-(3-Carboxy-5-methoxyacetamido-2,4,6-triiodobenzoyl)-sarcosine Methylamide

The above compound is produced in accordance with Example 11 from N-(3-carboxy-5-amino-2,4,6-triiodobenzoyl)sarcosine methylamide (IV e), m.p. 238°–239° C. (under decomposition), and in methoxyacetyl chloride.

Yield: 41%, m.p. 267°–269° C. (under decomposition).

Analysis: $C_{15}H_{16}I_3N_3O_6$ (715.0). Calculated: I 53.24%, E 715. Found: 53.24, 725.

EXAMPLE 31

N-(3-Carboxy-5-acetamido-2,4,6-triiodobenzoyl)-DL-valine Methylamide

As described in Example 1, N-(3-carboxy-5-amino-2,4,6-triiodobenzoyl)-DL-valine methylamide (IV p), m.p. about 235° C. (under decomposition), is reacted with acetyl chloride.

Yield: 82%, m.p. 259°–261° C. (under decomposition).

Analysis: $C_{16}H_{18}I_3N_3O_5$ (713.0). Calculated: C 26.95%, H 2.55%, N 5.89%, I 53.39%, E 713. Found: 26.40, 3.01, 5.73, 52.93, 717.

EXAMPLE 32

N-(3-Carboxy-5-methoxyacetamido-2,4,6-triiodobenzoyl)-DL-valine Methylamide

Analogously to Example 11, the above compound is prepared from N-(3-carboxy-5-amino-2,4,6-triiodobenzoyl)-DL-valine methylamide (IV p), m.p. about 235° C. (under decomposition), and methoxyacetyl chloride.

Yield: 65%, m.p. 285°–286° C. (under decomposition).

Analysis: $C_{17}H_{20}I_3N_3O_6$ (743.1). Calculated: C 27.48%, H 2.71%, N 5.66%, I 51.23%, E 743. Found: 27.77, 3.09, 5.86, 51.19, 745.

EXAMPLE 33

N-(3-Carboxy-5-acetamido-2,4,6-triiodobenzoyl)-L-valyl-L-valine Methylamide

This compound is obtained analogously to Example 1 by acetylation of N-(3-carboxy-5-amino-2,4,6-triiodobenzoyl)-L-valyl-L-valine methylamide (IV r), m.p. 247°–248° C. (under decomposition).

Yield: 67%, m.p. 255°–257° C. (under decomposition).

Analysis: $C_{21}H_{27}I_3N_4O_6$ (812.2). Calculated: C 31.05%, H 3.35%, N 6.90%, I 46.88%, H 818. Found: 30.07, 3.63, 6.79, 46.37, 815.

EXAMPLE 34

N-(3-Carboxy-5-acetamido-2,4,6-triiodobenzoyl)-N-phenyl-β-alanine Methylamide

Analogously to Example 1, the above compound is produced from N-(3-carboxy-5-amino-2,4,6-triiodobenzoyl)-N-phenyl-β-alanine methylamide (IV s), m.p. about 220° C. (under decomposition), and acetyl chloride.

Yield: 53%, m.p. 232°–234° C. (under decomposition).

Analysis: $C_{20}H_{18}I_3N_3O_5$ (761.1). Calculated: I 50.02%, E 761. Found: 49.01, 769.

EXAMPLE 35

N-(3-Aminocarbonyl-5-methoxyacetamido-2,4,6-triiodobenzoyl)-β-alanine

Analogously to Example 11, this compound is obtained from N-(3-aminocarbonyl-5-amino-2,4,6-triiodobenzoyl)-β-alanine (IX c), m.p. about 190° C. (under decomposition), and methoxyacetic acid/thionyl chloride.

Yield: 70%, m.p. 284°–285° C. (under decomposition).

Analysis: $C_{14}H_{14}I_3N_3O_6$ (701.0). Calculated: C 23.99%, H 2.01%, N 6.00%, I 53.31%, E 701. Found: 23.80, 2.52, 5.81, 54.22, 701.

EXAMPLE 36

N-(3-Methylaminocarbonyl-5-methoxyacetamido-2,4,6-triiodobenzoyl)glycine

As described in Example 11, this compound is obtained from N-(3-methylaminocarbonyl-5-amino-2,4,6-triiodobenzoyl)-glycine (IX a), m.p. 265°–266° C. (under decomposition), and methoxyacetyl chloride.

Yield: 55%, m.p. 310°–312° C. (under decomposition).

Analysis: $C_{14}H_{14}I_3N_3O_6$ (701.0). Calculated: C 23.99%, H 2.01%, N 6.00%, I 54.31%, E 701. Found: 24.05, 2.00, 6.00, 54.28, 690.

EXAMPLE 37

N-(5-Hydroxyacetamido-3-methylaminocarbonyl-2,4,6-triiodobenzoyl)-glycine

Analogously to Example 23, this compound is produced from N-(3-methylaminocarbonyl-5-amino-2,4,6-triiodobenzoyl)-glycine (IX a), m.p. 265°–266° C., and acetoxyacetyl chloride with subsequent saponification of the acetoxyacetyl residue.

Melting point of the product: 293°–295° C. (under decomposition).

Analysis: $C_{13}H_{12}I_3N_3O_6$ (687.0). Calculated: C 22.73%, H 1.76%, N 6.12%, I 55.42%. Found: 22.35, 1.88, 5.98, 55.32.

EXAMPLE 38

N-(3-Methylaminocarbonyl-5-acetamido-2,4,6-triiodobenzoyl)-glycylglycine

As described in Example 14, this compound is produced from N-(3-methylaminocarbonyl-5-amino-2,4,6-triiodobenzoyl)-glycylglycine (IX h), m.p. 245°–246° C. (under decomposition), and acetyl chloride in dimethylacetamide.

Yield: 41%, m.p. 241°–243° C. (under decomposition).

Analysis: $C_{15}H_{15}I_3N_4O_6$ (728.0). Calculated: I 52.29%, E 728. Found: 52.15, 725.

EXAMPLE 39

N-(3-Methylaminocarbonyl-5-methoxyacetamido-2,4,6-triiodobenzoyl)-sarcosine

The above compound is obtained analogously to Example 11 by the methoxyacetylation of N-(3-methylaminocarbonyl-5-amino-2,4,6-triiodobenzoyl)-sarcosine (IX g), m.p. 236°–237° C. (under decomposition), with methoxyacetyl chloride.

Yield: 76%, m.p. 299°–301° C. (under decomposition).

Analysis: $C_{15}H_{16}I_3N_3O_6$ (715.0). Calculated: I 53.24%, E 715. Found: 52.93, 710.

EXAMPLE 40

N-(3-Methylaminocarbonyl-5-methoxyacetamido-2,4,6-triiodobenzoyl)-DL-serine

Analogously to Example 11, this compound is prepared from N-(3-methylaminocarbonyl-5-amino-2,4,6-triiodobenzoyl)-DL-serine (IX e), m.p. 247°–248° C. (under decomposition), and methoxyacetic acid/thionyl chloride.

Melting point of this product: 269°–271° C. (under decomposition).

Analysis: $C_{15}H_{16}I_3N_3O_7$ (731.0). Calculated: N 5.75%, I 52.08%, E 731. Found: 5.72, 51.65, 730.

EXAMPLE 41

Preparation of a ready-for-use methylglucamine salt solution:

| | |
|---|---|
| N-(3-Carboxy-5-acetamido-2,4,6-triiodobenzoyl)-glycine methylamide | 669.2 g. |
| N-Methylglucamine | 194.5 g. |
| Disodium edetate | 0.1 g. |
| Twice-distilled water | ad 1000.0 ml. |

The solution is filled into ampoules or "multivials" and sterilized at 120° C. This solution contains 380 mg. I/ml.

EXAMPLE 42

Preparation of a ready-for-use sodium salt solution:

| | |
|---|---|
| N-(3-Carboxy-5-acetamido-2,4,6-triiodobenzoyl)-glycine methylamide | 669.2 g. |
| Sodium hydroxide | 39.9 g. |
| Disodium edetate | 0.1 g. |
| Twice-distilled water | ad 1000.0 ml. |

The solution is filled into ampoules or "multivials" and sterilized at 120° C. This solution contains 380 mg. I/ml.

EXAMPLE 43

Preparation of a ready-for-use methylglucamine salt solution:

| | |
|---|---|
| N-(3-Carboxy-5-acetamido-2,4,6-triiodobenzoyl)-DL-serine methylamide | 699.2 g. |
| N-Methylglucamine | 194.5 g. |
| Disodium edetate | 0.1 g. |
| Twice-distilled water | ad 1000.0 ml. |

The solution is filled into ampoules or "multivials" and sterilized at 120° C. This solution contains 380 mg. I/ml.

EXAMPLE 44

Preparation of a ready-for-use methylglucamine salt solution:

| | |
|---|---|
| N-(3-Carboxy-5-methoxyacetamido-2,4,6-triiodobenzoyl)-DL-serine methylamide | 537.6 g. |
| N-Methylglucamine | 143.6 g. |
| Disodium edetate | 0.1 g. |
| Twice-distilled water | ad 1000.0 ml. |

This solution is filled into ampoules or "multivials" and sterilized at 120° C. This solution contains 280 mg. I/ml.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes andd modifi-

What is claimed is:

1. A triiodoisophthalic acid monoamino acid amide of the formula

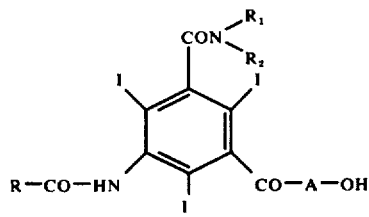

where A is a divalent amino lower alkanoyl linked to the carboxyl group via the amino acid nitrogen;

R is alkyl, hydroxyalkyl or alkoxyalkyl of 1-6 carbon atoms;

$R_1$ and $R_2$ are each hydrogen, alkyl of 1-6 carbon atoms or hydroxyalkyl of 2-6 carbon atoms, or $R_1$ and $R_2$ together with the nitrogen atom to which they are bonded form a 5 to 7 member heterocyclic ring which can contain a further oxygen or nitrogen hetero atom:

and the physiologically acceptable salts thereof.

2. A compound according to claim 1, wherein said amino acid nitrogen is a secondary nitrogen atom.

3. A compound according to claim 1 wherein said amino acid is a monoaminomonocarboxylic acid or a heterocyclic amino acid.

4. A claim according to claim 1 wherein one of $R_1$ $R_2$ is hydrogen.

5. A compound according to claim 1 in which

is morpholino, pyrrolidino or piperazino.

6. A compound according to claim 1, N-(3-methylaminocarbonyl-5-methoxyacetamido-2,4,6-triiodobenzoyl)-sarconsine.

7. A compound according to claim 1, N-(3-methylaminocarbonyl-5-methoxyacetamido-2,4,6-triiodobenzoyl)-DL-serine.

8. A compound according to claim 1 selected from the group consisting of N-(3-methylaminocarbonyl-5-acetamido-2,4,6-triiodobenzoyl)-β-alanine; N-(3-methylaminocarbonyl-5-acetamido-2,4,6-triiodobenzoyl)-sarcosine; N-(3-methylaminocarbonyl-5-acetamido-2,4,6-triiodobenzoyl)-DL-threonine; N-(3-aminocarbonyl-5-acetamido-2,4,6-triiodobenzoyl-α-alanine; N-(3-methylaminocarbonyl-5-acetamido-2,4,6-triiodobenzoyl)-DL-serine; and N-(3-aminocarbonyl-5-methoxyacetamido-2,4,6-triiodobenzoyl)-β-alanine.

9. A compound according to claim 1 selected from the group consisting of N-(3-methylaminocarbonyl-5-acetamido-2,4,6-triiodobenzoyl)-glycine and N-(3-methylaminocarbonyl-5-propionylamino-2,4,6-triiodobenzoyl)-glycine; N-(3-aminocarbonyl-5-acetamido-2,4,6-triiodobenzoyl)-glycine; N-(3-methylaminocarbonyl-5-methoxyacetamido-2,4,6-triiodobenzoyl)-glycine; and N-(3-methylaminocarbonyl-5-hydroxyacetamido-2,4,6-triiodobenzoyl)-glycine.

* * * * *